United States Patent
Shepherd et al.

(10) Patent No.: US 8,759,068 B2
(45) Date of Patent: Jun. 24, 2014

(54) SYSTEM FOR FERMENTATION USING ALGAE

(75) Inventors: Samuel L. Shepherd, Houston, TX (US); Jerry McCall, Houston, TX (US)

(73) Assignee: Missing Link Technologies, L.L.C., Houston, TX (US)

( * ) Notice: Subject to any disclaimer, the term of this patent is extended or adjusted under 35 U.S.C. 154(b) by 1278 days.

(21) Appl. No.: 12/115,384

(22) Filed: May 5, 2008

(65) Prior Publication Data
US 2009/0170184 A1 Jul. 2, 2009

Related U.S. Application Data

(60) Provisional application No. 61/018,620, filed on Jan. 2, 2008.

(51) Int. Cl.
| | |
|---|---|
| C12N 1/38 | (2006.01) |
| C12M 1/00 | (2006.01) |
| C12M 1/02 | (2006.01) |
| C12P 7/14 | (2006.01) |
| A01G 7/00 | (2006.01) |

(52) U.S. Cl.
USPC ............ 435/244; 435/293.1; 435/290.2; 435/294.1; 435/162; 47/1.4

(58) Field of Classification Search
USPC ........................... 435/292.1, 471.4
See application file for complete search history.

(56) References Cited

U.S. PATENT DOCUMENTS

| | | | |
|---|---|---|---|
| 4,069,149 A | 1/1978 | Jackson | |
| 4,286,066 A | 8/1981 | Butler et al. | |
| 5,516,423 A * | 5/1996 | Conoby et al. | 210/85 |
| 5,688,674 A | 11/1997 | Choi et al. | |
| 6,370,815 B1 * | 4/2002 | Skill et al. | 47/1.4 |
| 6,599,735 B1 | 7/2003 | Bartok et al. | |
| 2005/0035059 A1 * | 2/2005 | Zhang et al. | 210/605 |
| 2008/0086938 A1 * | 4/2008 | Hazlebeck et al. | 47/1.4 |
| 2009/0081743 A1 * | 3/2009 | Hazelbeck et al. | 435/157 |

* cited by examiner

*Primary Examiner* — Robert T Crow
*Assistant Examiner* — Joseph G Dauner
(74) *Attorney, Agent, or Firm* — Egbert Law Offices, PLLC

(57) ABSTRACT

The system for fermentation using algae of the present invention includes a first reactor and a second reactor being in fluid communication with each other. A first valve placed between the first reactor and the second reactor controls the fluid connection between the reactors. A gas inlet, in fluid connection to the first reactor, is located at an end opposite the second reactor. A devolatization unit or cell lysis chamber is connected to the second reactor by a second valve. A biomass stream having gas, liquid and biosolids contents passes through the first reactor with gas. The biomass stream mixes and dissolves the gas in the reactors. The cellular structure of the biomass stream ruptures in the devolatization unit, allowing the processed materials, such as oil, gas, and biosolids, to be harvested for use.

5 Claims, 5 Drawing Sheets

US 8,759,068 B2

SYSTEM FOR FERMENTATION USING ALGAE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to systems for fermentation. More particularly, the present invention relates to systems for fermentation using algae as the microorganism.

2. Description of Related Art

Including Information Disclosed Under 37 CFR 1.97 and 37 CFR 1.98.

From the simplest to the most complex, biological processes maybe classified as fermentation, elementary physiological processes, and the action of living organisms. Fermentation is a biological reaction whereby a raw organic material is converted into a product by the action of microorganisms or by the action of enzymes produced by microorganisms. In atypical fermentation reaction, a raw organic material is fed into a reactor. The raw organic material can be any carbon-based material including, but not limited to, carbon dioxide, sugar products, sewage sludge, animal manures and cellulosic materials. Once in the reactor, the raw organic material is mixed with microorganisms or microbes that are suitably chosen for a desired reaction with the raw organic material. The group of microorganisms or microbes includes, but is not limited to, yeasts, bacteria, algae, molds, and protozoa.

A reaction occurs whereby a product is formed by mixing the raw organic material with the microorganisms. This product depends on the type of raw organic material used as well as the type of microorganisms or microbes used. The product of the fermentation reaction is typically recovered from the biomass of the reaction through various separation methods such as dewatering and floatation.

Fermentation processes are known as autocatalytic processes. The autocatalytic behavior of a fermentation process is represented by a sequence of events. First, when the raw organic material is first introduced into the fermentation reactor, there is only a small amount of catalytic microorganisms present in the reactor. Thus, the conversion of the raw organic material into product is slow, i.e., the rate of reaction is very low. However, as the concentration, or number, of microorganisms increases, the reaction rate rises, producing more microorganisms and more products. In a typical fermentation reaction, the reaction rate reaches a maximum followed by a gradual die-off of the raw organic material. At this point, there is very little raw organic material and a lot of product, so the rate eventually slows until there is no reaction.

Because of their nature, fermentation reactions are typically carried out in a batch reactor. Batch reactors involve reacting a finite amount of material from start to completion and then starting over with a new finite amount of material in the reactor. This type of reactor is in contrast to a continuous reactor that continuously reacts a continuous supply of material. Because batch processes inevitably have a reaction that ends, they have a high operating cost, high capital cost, complicated sequencing, and limited production capabilities. Thus, there is a need for systems allowing for continuous fermentation that have improved operating cost, capital cost, and production capabilities over batch operations.

In the past, various patents have issued relating to systems for fermentation. For example, U.S. Pat. No. 6,599,735, issued on Jul. 29, 2003 to the Bartok et al., describes fermentation assembly comprising a vessel for culturing living cells, at least two storage flasks in fluid communication with the vessel for supply of liquids and a first transport means for transferring the liquids from the storage flasks to the vessel, individual appliances operably connected to the transport means for monitoring the supply of the contents of the storage flasks to the vessel, a harvest flask in fluid communication with the vessel and a second transport means for transferring the fermentation broth from the vessel to the harvest flask, and a device operably connected to the first transport means for controlling and maintaining a constant dilution rate in the vessel with varying rates of individual supply of liquid from the storage flasks to the vessel U.S. Pat. No. 5,688,674, issued on Nov. 18, 1997 to Choi et al., describes a metabolite, e.g., ethanol, that is continuously produced from low cost carbohydrate substrates by a process which comprises pulverizing the carbohydrate substrate, liquefying and saccharifying the pulverized substrate, continuously fermenting the lique-saccharified substrate in a fermentor equipped with a moving filter, in the presence of flocculent biological cells maintained at a concentration ranging from 90 to 160 g/l by using the moving filter and a culture medium to produce a fermentation product mixture, and recovering the desired metabolite from the fermentation product mixture.

U.S. Pat. No. 4,069,149, issued on Jan. 17, 1978 to Jackson, describes a deep-tank reactor utilized for fermentation of waste liquid or other liquid in a biological reaction resulting in a solid cellular material. The resulting solid material, which is in suspension, is initially separated from the bulk of the liquid by a gaseous flotation process, using the dissolved gas in the liquid as the source of gaseous bubbles for flotation purposes.

U.S. Pat. No. 4,286,066, issued on Aug. 25, 1981 to Butler et al., describes an apparatus for continuously fermenting a moist particulate feed and distilling the fermentation product where a pressure-locked auger forces a moist particulate feed from a hopper into a fermentation tank. Liquor is removed from the tank, and solids are separated therefrom to produce a beer which is distilled in a distillation column. A combustion engine powers the auger and the means for separating solids, and the engine exhaust surrounds an inlet section of said auger to help heat the pressurized feed therein to produce fermentable sugar within the auger, and the auger includes a section passing to the tank in heat exchange relation to the distillation column to provide heat for distillation. The column is a multistage column angled to face the sun and has an upper glass plate to allow solar radiation to enter and penetrate between the foraminous plates of the column.

It is an object of the present invention to provide a system for fermentation using algae.

It is another object of the present invention to achieve up to 80% reduction in the operating costs of batch fermentation processes.

It is another object of the present invention to provide a reactor design that optimizes fermentation reaction.

It is another object of the present invention to provide a system for fermentation of any raw organic material.

It is yet another object of the present invention to provide an optimal reactor design for any given set of operating conditions.

These and other objects and advantages of the present invention will become apparent from a reading of the attached specification.

BRIEF SUMMARY OF THE INVENTION

The present invention is a system for continuous fermentation using algae comprising at least one fermentation reactor having a first reactor section and a second reactor section. The first reactor section is a continuous stirred tank reactor and the second reactor section is a plug flow reactor. The first reactor section and the second reactor section are separated by a first baffle, the first baffle being movable within the fermentation reactor. The first reactor section has a second baffle that can be varied in size or shape so as to optimize the fermentation reaction within the first reactor section. In particular, the baffle of the second reactor position can be positioned for a residence time of up to seven days.

A dewatering means for removing water from the biomass product from the fermentation reactor is in fluid communication with the plug flow reactor of the second reactor section of the fermentation reactor. A cell lysis chamber is in fluid communication with the dewatering means, and a separator is in fluid communication with the cell lysis chamber. A storage tank is in fluid communication with the separator, and a mixing tank is in fluid communication with the dewatering means and with the cell lysis chamber and with the separator and with the fermentation reactor. An anaerobic digester is in fluid communication with the cell lysis chamber.

The continuous stirred tank reactor has an inlet and an outlet, and the plug flow reactor has an inlet and outlet. The inlet of the plug flow reactor is in fluid communication with the outlet of the continuous stirred tank reactor. The first baffle separating the continuous stirred tank reactor and the plug flow reactor is movable and has an opening therein, and the opening is coincident with the outlet of the continuous stirred tank reactor and the inlet of the plug flow reactor. The baffle can be moved within the fermentation reactor so as to adjust the size of the continuous stirred tank reactor and the volume of the plug flow reactor for optimal conditions for reacting a given raw feed material. The plug flow reactor is impervious to light. The plug flow reactor has a residence time of up to seven days.

After the dewatering means water is sent to the mixing tank, it is further mixed with additional water, nutrients, and carbon dioxide. The dewatered biomass from the dewatering means is sent to the cell lysis chamber where product is removed from the biomass. The biomass is sent to the anaerobic digester and the product is sent to the separator where water is removed from oil. The water that is removed from the product goes to the mixing tank, and the product goes to the storage tank. The water that is mixed with new water, nutrients, and carbon dioxide in the mixing tank is recycled back to the fermentation reactor. Biogas is recovered from the biomass in the anaerobic digester.

In another embodiment of the invention, the system for fermentation using algae comprises a first reactor having a generally cylindrical shape and a biomass inlet and a second reactor being in fluid communication with the first reactor. A first valve means is placed between the first reactor and the second reactor to control the fluid connection between the first reactor and the second reactor. A gas inlet, in fluid connection to the first reactor, is located at an end opposite the second reactor. A compressor unit and gas source are in fluid connection with the gas inlet. A devolatization unit is connected to the second reactor by a second valve means and has a transfer pump and a gas line. The gas line connects to the compressor, while the second valve means controls fluid connection between the second reactor and the devolatization unit. The gas source is a carbon dioxide supply. The first reactor having a mixing nozzle within an interior volume thereof.

The method for fermentation using algae, for this embodiment includes injecting gas into a biomass stream containing oil, a liquid portion, a solid portion. The gas is dissolved into the biomass stream under mixing conditions in the first reactor. The biomass stream mixture transfers into a second reactor where the gas is defused into the cellular structure of the biomass stream. The biomass stream mixture passes through a second valve, so that the gas changes phase from liquid to vapor within the biomass cellular structure and ruptures the cellular structure. The depressurized mixture is conveyed to a devolatization unit, wherein the gas, the oil, and the solids being separated. The oil is skimmed from the surface of the depressurized mixture, the gas is recycled though a gas line, and the solids are removed by a transfer pump.

DETAILED DESCRIPTION OF THE INVENTION

Figure 1:
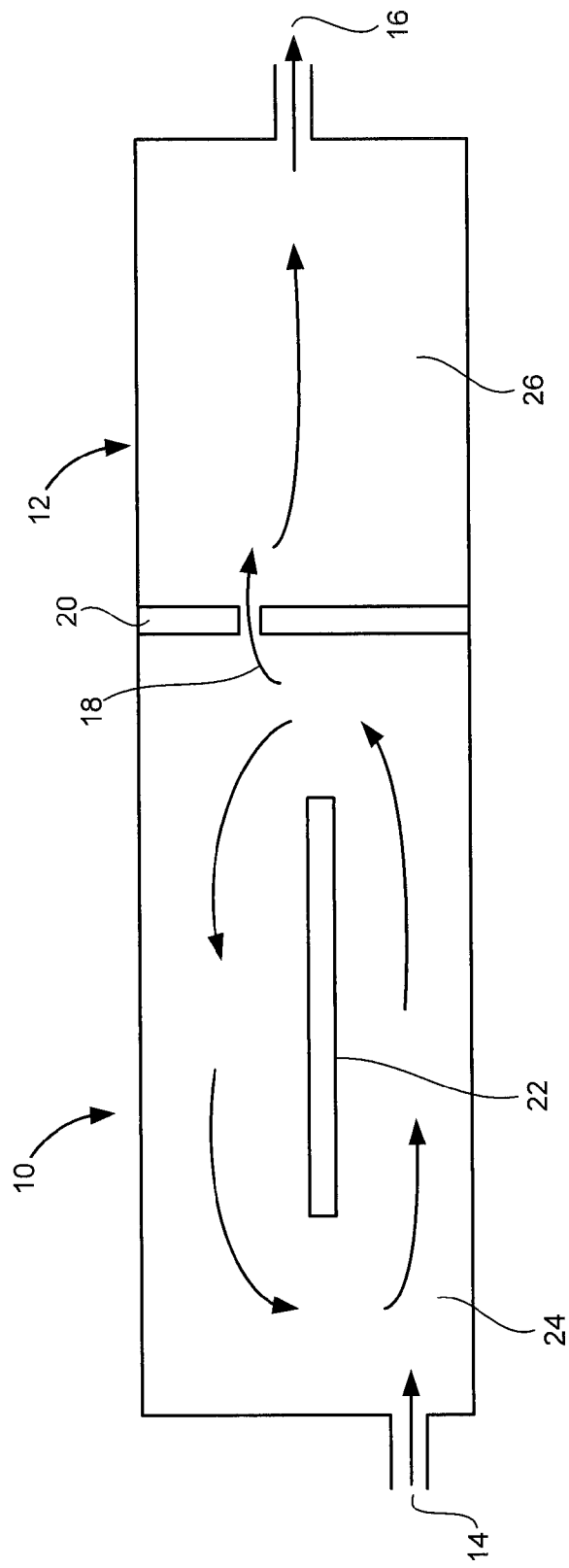
FIG. 1 is a cross-sectional view of the reactor for fermentation using algae of the present invention.

Referring to FIG. 1 there is shown the fermentation reactor 10 in accordance with the teachings of the preferred embodiment of the present invention. The fermentation reactor 10 includes a first reactor section 24 and a second reactor section 26 separated by a baffle 20. The first reactor section 24 is a continuous stirred tank reactor, and the second reactor section 26 is a plug flow reactor. The first reactor section 24 has an inlet 14 where raw organic materials, microorganism, and recycled biomass are continuously fed. In the preferred embodiment, the microorganism is algae. The raw organic materials, algae, and recycled water are together called reacting mass, and this reacting mass is mixed in the first reactor section 24 using recycling, recirculating, or mechanical mixing techniques. The reaction in the first reactor section 24 involves growing algae at temperatures ranging from 40° F. to 180° F. and at pressures ranging from 0.8 bar to 8 bar. The reaction in the second reactor section 26 involves transferring biomass into the plug flow reactor of the second reactor section 26 whereby the biomass converts, in the absence of light, carbohydrates into oil. This reaction increases the oil content of the biomass. This reaction occurs over a period of up to seven days. That is, the residence time of the second reactor section 26 is up to seven days.

A baffle 22 is received within the first reactor section 24 and can be varied vertically and horizontally within the first reactor section 24 so as to optimize the fermentation reaction. Baffle 20 has an opening 18 where biomass in the first reactor section 24 passes to the second reactor section 26. The second reactor section 26 has an outlet 16 where the biomass exits the fermentation reactor 10. Baffle 20 is movable along the inner walls 28 of the fermentation reactor 10 so as to vary the volumes of the first reactor section 24 and the second reactor section 26. Varying the volumes allows one to change the residence times in the first reactor section 24 and the second reactor section 26 so as to optimize the fermentation reaction for a raw organic material. The rate equation used to optimize the design for the fermentation reactor 10 is:

$$-rA = k_1 * C_c * (C_A/(k_2 + C_A))$$

where k1 and k2 are constants, Cc is the concentration of the microorganisms in the fermentation reactor 10, CA is the concentration of the raw organic material, and rA is the rate of reaction. This rate equation implies a shift from a "zeroeth" order rate equation at high concentrations of CA to a "first" order equation at low concentrations of CA. Therefore, the fermentation reactor 10 of the present invention allows for an optimal reactor design for a given set of operating conditions through manipulation of the baffles 20 and 22. In the preferred embodiment, the baffle 20 should be placed so as to have a residence time of seven days in the second reactor section 26.

Figure 2:
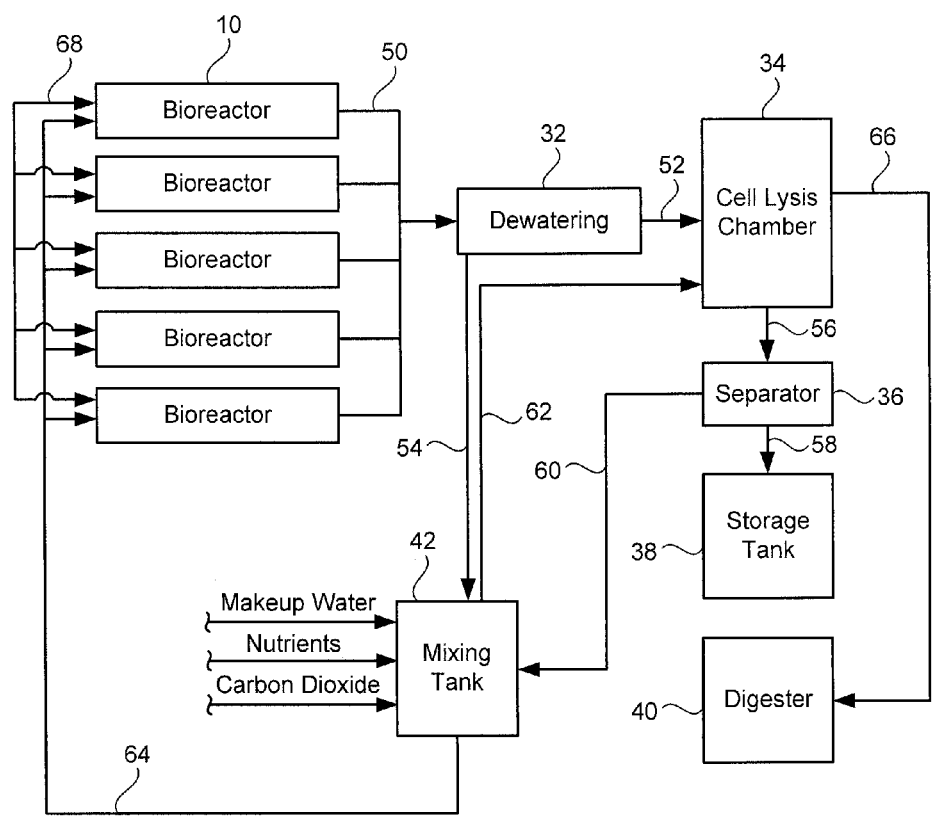
FIG. 2 is a schematic illustration of the fermentation process utilizing the fermentation reactor of the present invention.

Referring to FIG. 2, there is shown a plurality of fermentation reactors 10 coordinated with the product recovery process. Raw organic material and algae are fed into the reactors 10 through line 68. Biomass product exits from the fermentation reactor 10 and travels in line 50 to the dewatering means 32. Water is removed from the biomass in the dewatering means 32 by centrifuge, belt press, or floatation techniques so that the biomass contains only 2% to 50% water. The water is sent to the mixing tank 42 through line 54. Biomass from the dewatering means 32 is sent to the cell lysis chamber 34 through line 52. The biomass in the cell lysis chamber 34 is mixed with carbon dioxide from line 62 at a pressure exceeding 1 bar. The purpose of the cell lysis chamber 34 is to recover product from the biomass by disrupting the microorganism structure thereby releasing the desired product in the aqueous phase.

Product recovered in the cell lysis chamber 34 is sent to the separator 36 by line 56. Biomass leaving the cell lysis chamber 34 travels to the anaerobic digester 40 by line 66. The biomass could also be collected for food or a biomass fuel through line 66. Product from the cell lysis chamber 34 is separated from the aqueous phase in the separator 36 by centrifuge, distillation, or decanting techniques. Water is removed in the separator 36 and sent to the mixing tank 42 by line 60. Product recovered in the separator 36 is sent to the storage tank 38 by line 58. It is possible to send the product from the separator 36 through an activated carbon bed or to crystallize the product so as to further recover the desired product before sending product to the storage tank 38. Biomass is separated into Biogas and biomass in the anaerobic digester 40.

Water from the dewatering means 32 and separator 36 that goes to the mixing tank 42 by lines 54 and 60, respectively, is mixed with makeup water 44, nutrients 46, and carbon dioxide 48. The mixed water is then recycled to the fermentation reactor 10 by line 64 where it is mixed with raw organic material and microorganisms so as to help sustain an equilibrium reaction rate.

As can be seen in FIG. 2, the process is continuous where raw organic material is fed to the fermentation reactors 10. Biomass is sent through the various process devices, water is recovered from these processes, recovered water is enriched with nutrients and carbon dioxide is recycled back to the fermentation reactors 10, and product is recovered in the storage tank 38.

The present invention contemplates varying the feed rates of the raw organic material to control the rate of reaction according to the rate equation given above. The present invention also contemplates using light filtering, consisting of reflective panels, opaque glass, light filters, or any other apparatus, to allow light frequencies ranging from 600 nm to 780 nm to enter the fermentation reactor 10. When light is used for reaction in the fermentation reactor 10, the present invention contemplates varying the hours of light and dark to achieve the optimal reaction rate and to minimize light toxicity. For example, in fermentation using algae, having a residence time of seven days in the absence of light in the second reactor section 26 of the fermentation reactor 10, i.e. the plug flow reactor of the present invention, increases the production of oil from the algal biomass.

Figure 3:
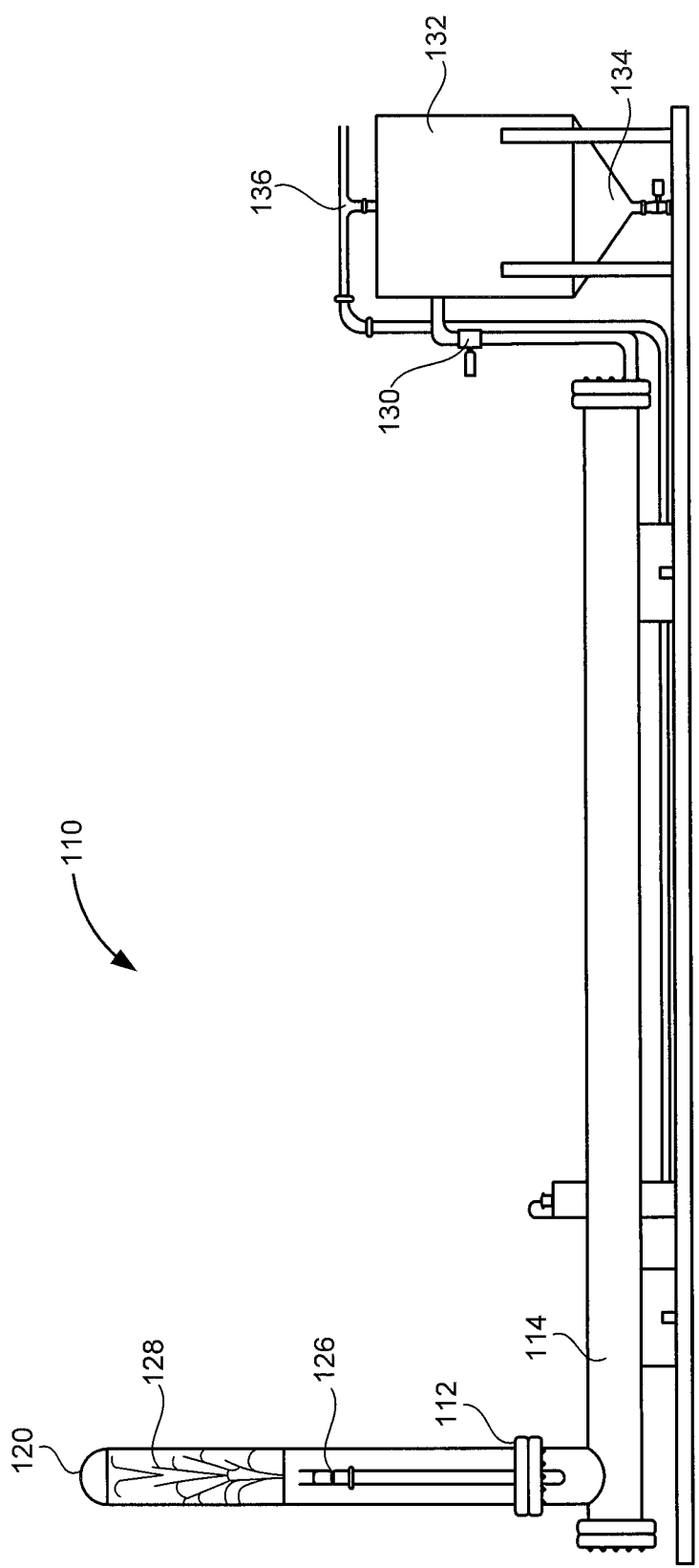
FIG. 3 is side elevation view of the system for the fermentation process according to another embodiment.
Figure 4:
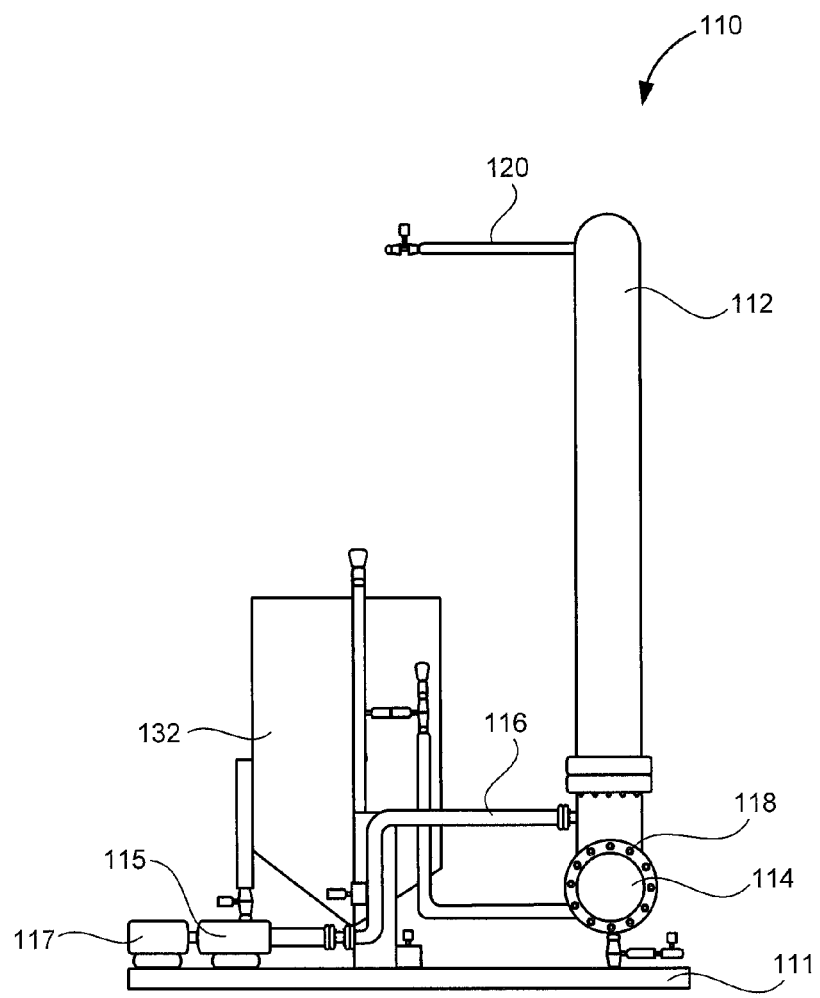
FIG. 4 is a front elevation view of the system for the fermentation process according to the embodiment of FIG. 3
Figure 5:
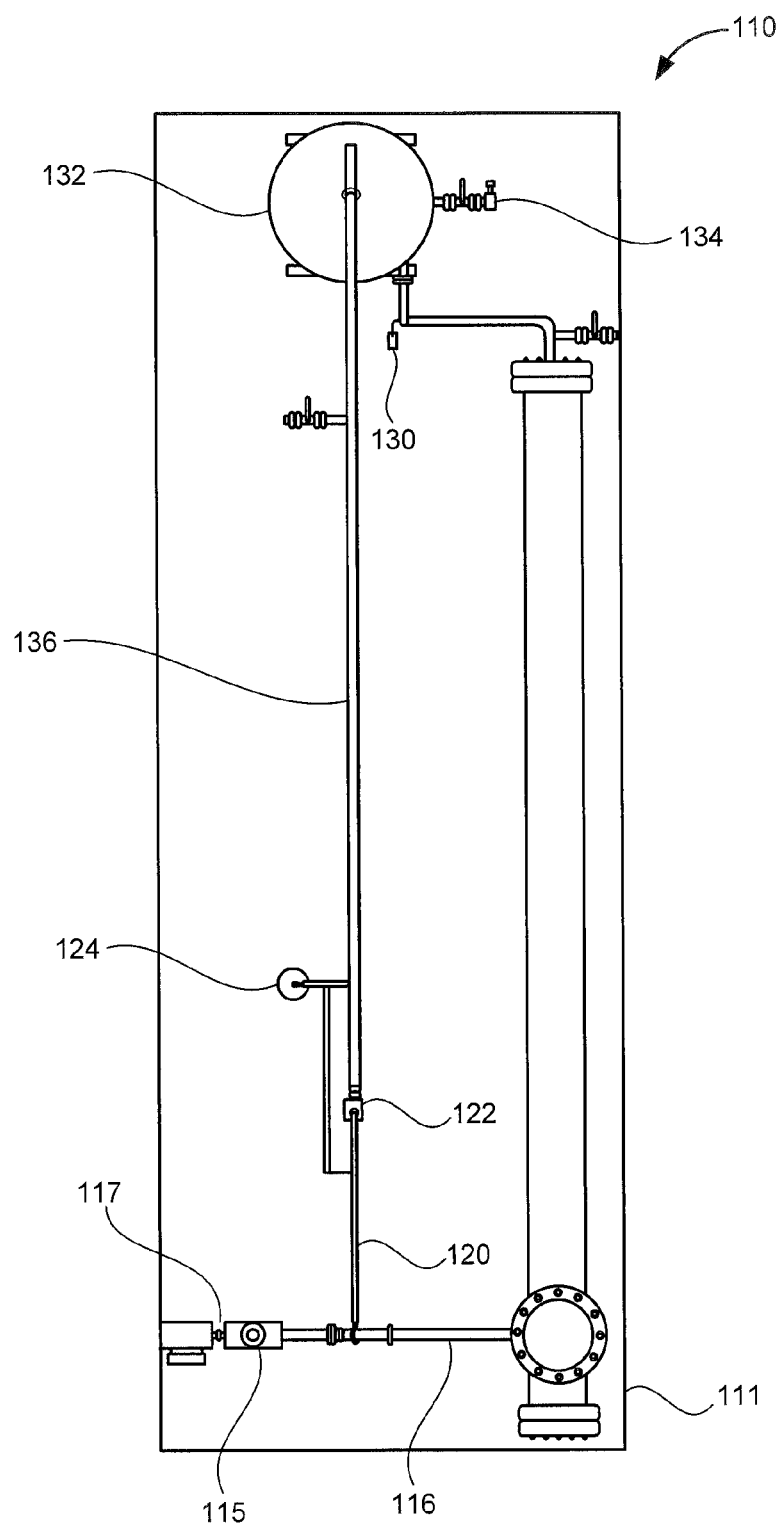
FIG. 5 is a top plan view of the system for the fermentation process according to the embodiment of FIG. 3.

FIGS. 3-5 show another embodiment 110 of the system of the present invention mounted on a platform 111. Instead of a single fermentation reactor 10, this embodiment has a first reactor 112 and a second reactor 114. The first reactor 112 has a generally cylindrical shape and a biomass inlet 116. The biomass inlet 116 receives the processed biomass stream, such as algae, from a bioreactor 117 through a pump 115 into the first reactor 112. The second reactor 114 is in fluid communication with the first reactor 112 and is placed in an orthogonal relationship to the first reactor 112. A first valve means 118 placed between the first reactor 112 and the second reactor 114 controls fluid flow between the first reactor 112 and the second reactor 114.

The biomass stream entering the first reactor 112 has gas injected therein through a gas inlet 120 in fluid connection with the first reactor 112. The gas inlet 120 is located at one end of the first reactor 112, and the biomass inlet 116 is located at the other end of the first reactor. Both the gas inlet 120 and the biomass inlet 116 are orthogonal to the first reactor 112 and the second reactor 114. A compressor unit 122 in fluid connection with the gas inlet 120 pressurizes the biomass stream in the first reactor 112. The gas source 124 connected to the gas inlet 120 is carbon dioxide gas. The first reactor 112 has a mixing nozzle 126 within an interior volume 128 of the first reactor 112, insuring a proper mixture and dissolving of the gas source 124 into the liquid portion of the biomass stream. The contents are maintained at a pre-set level in the first reactor 112.

The biomass stream passes through first valve means 118 to the second reactor 114 for the diffusion of the $CO_2$ gas into the cellular structure of the biomass stream. After a predetermined amount of time in second reactor 114, the biomass stream passes through a second valve means 130 to a devolatization unit 132. The change in pressure from second reactor 114 through the second valve means 130 to the devolatization unit 132 causes the $CO_2$ gas to change phase from liquid to gas within the biomass cellular structure. The cells are ruptured, releasing a mixture of gas, oil, water, and biosolids. A transfer pump 134 and gas line 136 connected to the devolatization unit 132 separate the contents for re-use in the system. For example, the $CO_2$ gas can be returned to the gas inlet 120, and the biomass solids can be released through transfer pump 134 for further processing in anaerobic digestion or fermentation into ethanol. Importantly, the oil can be skimmed from the surface of the biomass mixture as fuel. It is an object of the present invention to provide a system for fermentation using algae.

The present invention achieves up to 80% reduction in the operating costs of a batch fermentation processes because the process is continuous. The fermentation reactor of the first embodiment optimizes fermentation reaction between the first and second sections. The system applies to fermentation of any raw organic material and adjusts the first and second section for an optimal reactor for any given set of operating conditions.

Additionally, the present invention provides an efficient resource for production of oil, an alternative to naturally occurring oil that must be harvested from the Earth. The present invention uses the biological processing of microorganisms, specifically algae, to process waste products, while creating usable resources. The present invention allows for the efficient or maximized collection of oil from the biological processing.

The foregoing disclosure and description of the invention is illustrative and explanatory thereof. Various changes in the details of the described system and method can be made within the scope of the appended claims without departing from the true spirit of the invention.

We claim:

1. A system for fermentation using algae comprising:
   at least one fermentation reactor having a first reactor section and a second reactor section, said first reactor section being a continuous stirred tank reactor, said second reactor section being a plug flow reactor;
   a first baffle separating said first reactor section and said second reactor section and being movable within the fermentation reactor,
   a dewaterer in fluid communication with said second reactor section so as to remove water from a biomass product from the fermentation reactor;
   a cell lysis chamber being in fluid communication with said dewaterer;
   a separator being in fluid communication with said cell lysis chamber;
   a storage tank being in fluid communication with said separator;
   a mixing tank being in fluid communication with said dewaterer, said cell lysis chamber, said separator, and said fermentation reactor; and
   an anaerobic digestor being in fluid communication with the cell lysis chamber, wherein said first reactor section has a second baffle of a variable size or shape so as to optimize the fermentation reaction within the first reactor section.

2. The system according to claim 1, wherein said first reactor section having an inlet and an outlet, said second reactor section having an inlet and outlet, said inlet of said second reactor section being in fluid communication with said outlet of said first reactor section, said second reactor section being movable and having an opening therein, said opening coinciding with said outlet of said first reactor section and said inlet of said second reactor section.

3. The system according to claim 1, wherein said first baffle being moveable within said first reactor section such that said first reactor section and said second reactor section have adjustable volumes.

4. The system according to claim 1, wherein said second reactor section being impervious to light.

5. A system for fermentation using algae comprising:
   at least one fermentation reactor having a first reactor section and a second reactor section, said first reactor section being a continuous stirred tank reactor, said second reactor section being a plug flow reactor;
   a first baffle separating said first reactor section and said second reactor section and being movable within the fermentation reactor,
   a dewaterer in fluid communication with said second reactor section so as to remove water from a biomass product from the fermentation reactor;
   a cell lysis chamber being in fluid communication with said dewaterer;
   a separator being in fluid communication with said cell lysis chamber;
   a storage tank being in fluid communication with said separator;
   a mixing tank being in fluid communication with said dewaterer, said cell lysis chamber, said separator, and said fermentation reactor; and
   an anaerobic digestor being in fluid communication with the cell lysis chamber, wherein said first baffle having a first reactor position and a second reactor position, said second reactor position providing a residence time of up to seven days.

* * * * *